United States Patent [19]

Morrill

[11] 4,140,111
[45] Feb. 20, 1979

[54] HAND TOOL FOR INSERTING BONE FRACTURE PINS

[76] Inventor: William E. Morrill, Rte. 32, North Franklin, Conn. 06254

[21] Appl. No.: 831,077

[22] Filed: Sep. 6, 1977

[51] Int. Cl.² ............... A61F 5/04; A61B 17/16
[52] U.S. Cl. ............... 128/92 E; 128/305.1; 81/3 R; 145/53
[58] Field of Search ........... 128/92 E, 92 EC, 83, 128/303 R, 305, 305.1, 310; 81/3 J, 3 R; 145/53; 408/703

[56] References Cited

U.S. PATENT DOCUMENTS

| 3,049,018 | 8/1962 | Lusskin et al. ............ 145/53 X |
| 3,351,054 | 11/1967 | Florek ...................... 128/83 |

FOREIGN PATENT DOCUMENTS 455567  2/1928  Fed. Rep. of Germany ............ 145/53

OTHER PUBLICATIONS

Der Chirurg, vol. 36, No. 5, pp. 231-232.

Primary Examiner—Ronald L. Frinks
Attorney, Agent, or Firm—Albert W. Hilburger

[57] ABSTRACT

A hand tool for inserting intramedulary pins in fractured bones of humans and animals. The tool includes an outer sleeve, a hollow shaft coaxially aligned within the sleeve having a continuous spiral groove in its outer surface, a cam follower on the outer sleeve slideably engaged with the spiral groove, a chuck mounted on one end of the shaft adapted to releasably grip an intramedulary pin, and a spring extended between the opposite end of the shaft and a flange integral with the hollow shaft. The tool is constructed to receive intramedulary pins of a variety of diameters and lengths. Additionally, it can be readily disassembled for its sterilization and for interchangeability of springs having different spring rates. As a person using the tool applies force to the sleeve to advance the pin longitudinally, the chuck is rotated and, with it, the pin which aids the insertion procedure.

9 Claims, 4 Drawing Figures

HAND TOOL FOR INSERTING BONE FRACTURE PINS

BACKGROUND OF THE INVENTION

This invention relates generally to hand tools and, more particularly, to a hand operated tool for inserting intramedulary pins into fractured bones of humans and animals.

In medical practice, it has become customary in certain situations to insert stainless steel pins into bone structure during orthopedic treatment. This may be accomplished by a physician operating upon a human or by a veterinarian operating upon an animal in those instances where it is desirable to provide internal support or fixation for the fractured bone.

For this purpose, hand tools have been employed to insert the steel pins into the bones or lined-up fragments of bones to be joined. The pin is inserted into a cavity within the bone called the medulary or marrow cavity. The bone subsequently heals around the pin but the pin served to stabilize the bone fragments while permitting the animal or human patient limited use of the limb so joined.

It has been the practice to insert intramedulary pins by means of a tool which firmly clamped the pin but required the operator to manually twist or rotate the tool and, with it, the pin as longitudinal force was applied to the tool. This combined action of longitudinal force on the pin together with its simultaneous rotation has been found to be of distinct advantage in the procedure of inserting pin into the bone marrow. However, such combined manual action made it difficult for the operator to assure that the pin was maintained in a desired direction as it advanced longitudinally. Rather, it often resulted in a wobbling motion which would adversely affect the final positioning of the bones being joined and would also result in drilling a hole in the bone of larger diameter than desired or needed to receive the pin.

In most instances, the hand tools previously employed did not allow for wide varieties of diameters and lengths of pins. Furthermore, they were usually of a complicated design which caused them to be expensive to fabricate and maintain. Additionally, tools of this type which have been used previously could not be readily disassembled for purposes of cleaning and sterilization and oftentimes required lubrication which further impeded such efforts.

SUMMARY OF THE INVENTION

The present invention serves as an improvement of these prior tools and, to this end, includes an outer sleeve, a hollow shaft coaxially aligned within the sleeve having a continuous spiral groove in its outer surface, a cam follower on the outer sleeve slideably engaged with the spiral groove, a chuck mounted on one end of the shaft adapted to firmly but releasably grip an intramedulary pin, and a spring extended between the opposite end of the shaft and a flange integral with the hollow shaft. This construction, contrary to previously known tools employed for inserting intramedulary pins, serves to achieve rotary motion of the pin in an automatic fashion as the operator applies longitudinal force to the tool. This enables the operator to continue the procedure without removal of his hand from the tool as was previously necessary in order to achieve the twisting motion. Additionally, the force is continuous and in a substantially direct line for joining the fractured bone ends.

The tool of this invention is constructed to receive intramedulary pins having a variety of diameters and lengths. Additionally, it can be readily disassembled for sterilization and for interchangeability of springs having different spring rates. This latter feature permits a wide range of operability of the tool consistent with the hardness of the bone structure to which a pin is to be applied. By reason of its construction and choice of materials, the tool requires no lubrication which is important for permitting sterilization of the tool.

Another feature of the invention is the ability of the operator to releasably hold the shaft and the sleeve in an intermediate position with the spring partly compressed in the event it should be desirable to temporarily halt the procedure. In this manner, the procedure can be resumed at the same stage at which it had been temporarily halted.

As utilized, the tool of the present invention enables the operator to attend to the pin insertion procedure employing only one hand. At the same time, the tool permits the drilling procedure to proceed in a precisely correct direction and without excessive wobble of the tool. The operator grips the handle of the tool and presses in the direction of the longitudinal axis of the pin. With continued force being applied by the operator, the chuck is caused to rotate and with it the pin which aids in insertion of the pin into the bone marrow. The spring element serves as a cushioning device between the handle and the chuck and is chosen in accordance with the hardness of the bone structure being united. Specifically, softer bones require a spring having a lower spring rate while harder bones require a spring having a higher spring rate.

It is to be understood that both the foregoing general description and the following detailed description are exemplary and explanatory but are not restrictive of the invention.

The accompanying drawings, which are incorporated in, and constitute a part of this invention illustrate a preferred embodiment of the invention, and together with the description serve to explain the principles of the invention.

OF THE DRAWINGS

DESCRIPTION OF THE PREFERRED EMBODIMENTS

Figure 1:
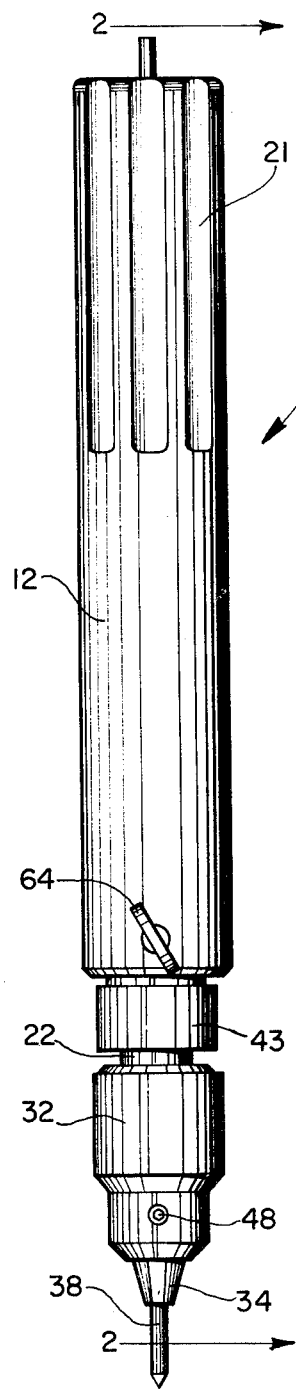
FIG. 1 is a side elevation view of the present invention.

Turn now to the drawings and initially to FIG. 1 which illustrates the outward appearance of a hand tool 10 having the characteristics of the present invention. In accordance with the invention, the hand tool 10 comprises an elongated hollow sleeve open at its opposite ends including flange means adjacent one of said ends projecting into the interior thereof; a hollow shaft removably supported within said sleeve and substantially coaxial therewith having at least one continuous spiral groove in its outer surface intermediate its ends; follower means removably secured to said sleeve and slideably engagable with the spiral groove on said shaft to effect rotation of the shaft in response to relative longitudinal movement between said sleeve and said shaft; chuck means having an axial opening therethrough and removably mounted to one end of said shaft for releasably clamping an elongated pin for rotation with said shaft, said shaft having a longitudinal bore therethrough communicating with the axial opening in said chuck means; and resilient means extending between said flange means and an end of said shaft opposite said chuck means.

Figure 2:
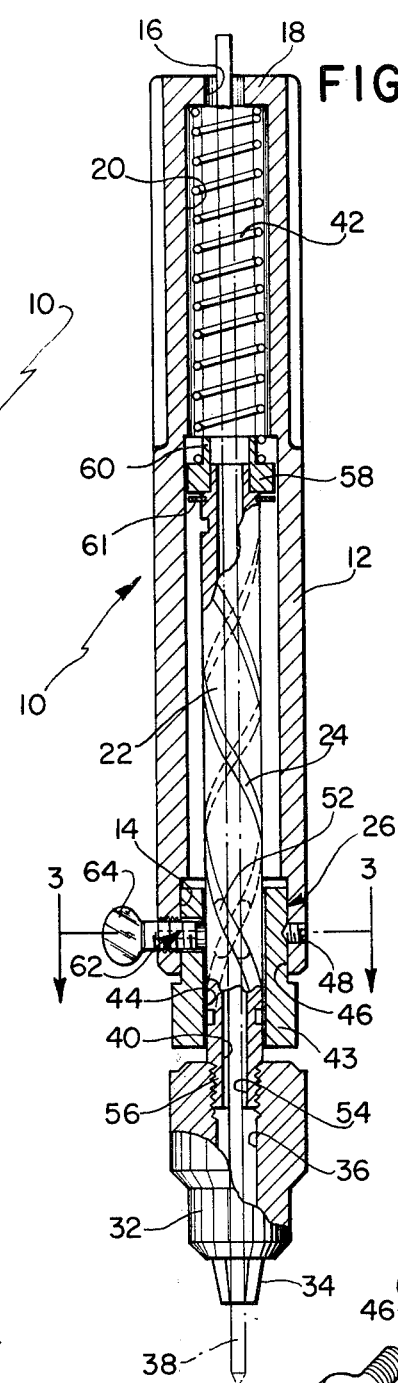
FIG. 2 is a section view, taken generally along line 2—2 in FIG. 1.

As embodied herein, as particularly well seen in FIG. 2, the hand tool 10 is provided with an elongated hollow sleeve 12 having an opening 14 at its lower end and an opening 16 at its upper end. Flange means 18 may be described as a rim defined between the opening 16 and inner surface 20 of the sleeve 12 at its upper end. As an aid in permitting a user to firmly grip the hand tool 10, a grooved handle portion 21 may be suitably formed on the outer surface of the sleeve 12 adjacent its upper end.

Figure 3:
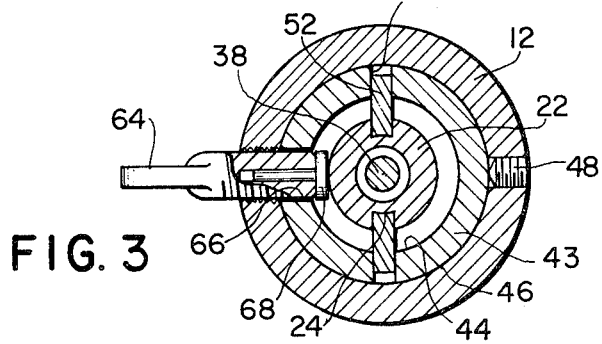
FIG. 3 is a section view taken generally along line 3—3 in FIG. 2.

Continuing with the construction illustrated in FIG. 2, a hollow shaft 22 is positioned within the sleeve 12 and substantially coaxial with the sleeve (see FIG. 3). At least one continuous spiral groove 24 is formed in the outer surface of the hollow shaft 22 and extends substantially from one end of the shaft to the other.

A follower mechanism 26 is releasably secured to the sleeve 12 in a manner which will be described below and including specific structure also to be described below is slideably engagable with the spiral groove 24 on the shaft 22 to effect rotation of the shaft in response to longitudinal movement between the sleeve 12 and the shaft 22.

A chuck mechanism 32 may be of any suitable design including a set of jaws 34 which communicate with an axial opening 36 adapted to releasably clamp elongated intramedulary pins 38 having any one of a wide range of diameters. The chuck mechanism 32 is suitably mounted on a lower end of hollow shaft 22 so that the axial opening 36 of the chuck mechanism 32 is able to communicate with a longitudinal bore 40 extending the length of the shaft 22.

Resilient means which may take the form of a spring 42 extend between the flange means or rim 18 and an upper end of the shaft 22 opposite the chuck mechanism 32.

Figure 4:
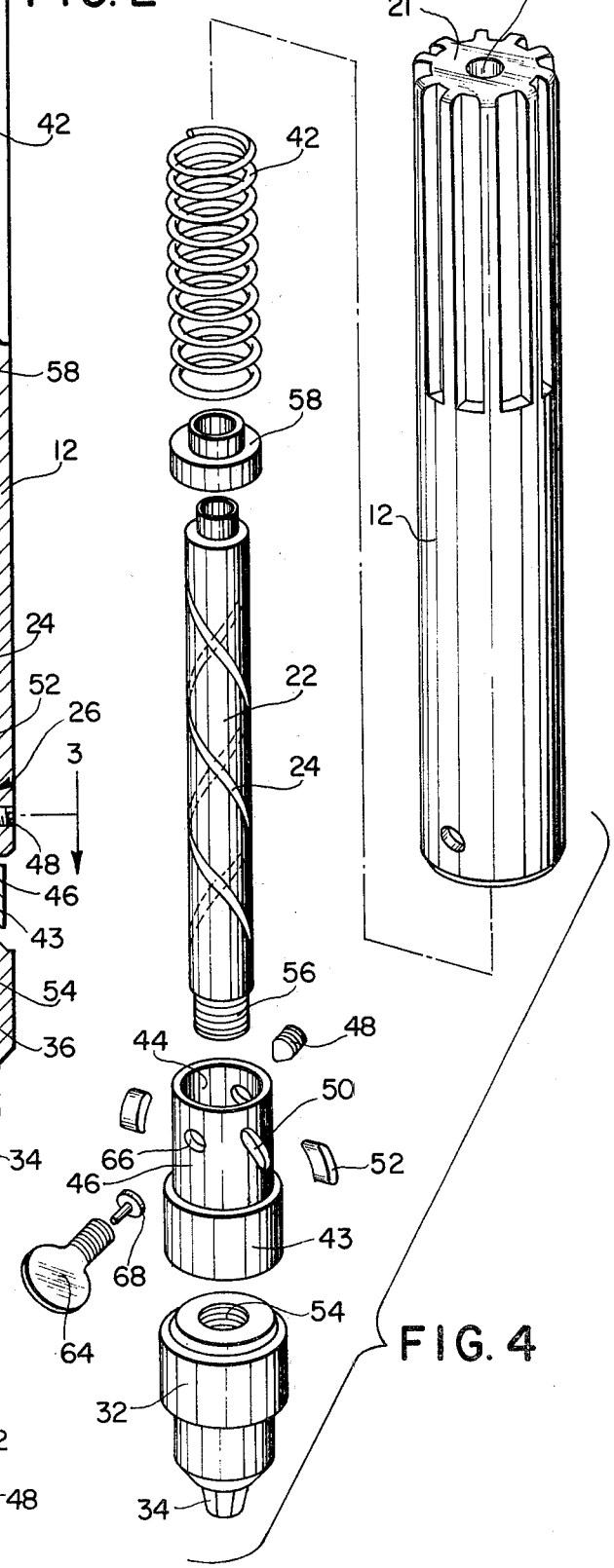
FIG. 4 is an exploded view, in perspective, illustrating the elements of the invention.

In accordance with the invention the follower mechanism 26 includes a bushing having a central bore extending therethrough and an outer peripheral surface and at least partially receivable within an end of said hollow sleeve opposite said flange means and a set screw threadedly engaged with said hollow sleeve and selectively engagable with said outer peripheral surface to releasably secure said bushing to said hollow sleeve. As embodied herein, and continuing to view FIG. 2, a bushing 43 is provided with a central bore 44 extending the length of the bushing and is further provided with an outer peripheral surface 46 (see FIG. 4) which is snugly received within the opening 14 at the lower end of the hollow sleeve 12. The bushing 43 is preferably fabricated of Teflon (trademark for polytetrafluoroethylene) or other similar suitable material capable of functioning without lubrication. It will be appreciated that the bushing 43 serves as a journal for the shaft 22 with resultant rubbing between the outer surface of the shaft and the inner surface of the bushing. With the bushing 43 fabricated of Teflon, frictional losses are held to a minimum without need for lubrication. A set screw 48 is threadedly engaged with the sleeve 12 and extends in a radial direction so that its base is selectively engagable with the outer peripheral surface 46 of the bushing 43. In this manner, the set screw 48 serves to releasably secure the bushing 43 to the hollow sleeve 12.

In accordance with the invention, the bushing 43 has a slot extending radially therethrough from its central bore to said outer peripheral surface and including a key within the slot and engaged with said spiral groove. As embodied herein, still viewing FIG. 2, bushing 43 is provided with at least one slot 50 (see FIG. 4) which extends radially through the bushing from its central bore 44 to its outer peripheral surface 46. A key 52 is receivable within the slot 50 and engagable with the spiral groove 24. It will thus be appreciated that with the bushing 43 held by the set screw 48 in a unitary fashion with the hollow sleeve 12 and with the key 52 confined within the slot 50 and held in engagement with the spiral groove 24 by that portion of the sleeve 12 located adjacent the opening 14, relative longitudinal movement of the sleeve 12 and the shaft 22 will result in rotation of the shaft relative to the sleeve. More specifically, any force imparted by an operator to the sleeve 12 along a longitudinal axis of the hand tool 10 will result in the key 52 bearing against the sidewall of the spiral groove 24 with resultant rotation of the shaft 22 relative to the sleeve 12.

In accordance with the invention, at least a portion of the axial opening of said chuck means is threaded and one end of said hollow shaft is a stud threadedly engaged with the axial opening of said chuck means. As embodied herein, with continued reference to FIG. 2, at least a portion of the axial opening 36 is provided with threads 54 for receiving a stud 56 integral with the lower end of the hollow shaft 22. Thus, the chuck mechanism 32 can be readily attached to or detached from the hollow shaft 22.

In accordance with the invention, the hand tool 10 includes a support bushing freely mounted on an end of said hollow shaft opposite said chuck means, said resilient means extending between said flange means and said bushing. As embodied herein, again with reference to FIG. 2, a support bushing 58 is provided at an upper end of the hollow shaft 22 opposite the chuck mechanism 32. The support bushing 58 serves as a seat for the lower end of the spring 42 and also serves as a journal bearing for support of the shaft 22 at its extreme end. The support bushing permits the shaft 22 to rotate freely without interfering with or interference from the spring 42.

It will also be noted that the support bushing 58 includes a rim portion having an outer diameter slightly smaller than the inner diameter of the sleeve 12. In this fashion, the support bushing 58 and the bushing 43 cooperate to maintain the axial alignment of the shaft 22 within the sleeve 12 regardless of the extent to which the spring 42 is compressed. Support bushing 58 is also desirably provided with an extension 60 receivable within the inner diameter of the spring and thus serves to prevent lateral movement or buckling of the spring relative to the shaft 22. For the same reasons recited with respect to the bushing 43, the support bushing 58 is also preferably fabricated of Teflon or other suitable material capable of functioning without lubrication.

A c-ring 61 having an outer diameter in the relaxed state greater than the inner diameter of the bushing 43 is preferably fixed to the shaft 22 adjacent the support bushing 58. In this manner, the c-ring 61 and the upper end of the bushing 43 (FIG. 2) define the lowermost travel of the shaft 22 relative to the sleeve 12 except when the tool 10 is in a condition of being disassembled.

In accordance with the invention, the hand tool 10 includes locking means selectively operable for holding said hollow shaft and said hollow sleeve against relative movement. As embodied herein with continued reference to FIG. 2, a locking mechanism generally indicated at 62 includes a thumb screw 64 threadedly received in a radial direction through the sleeve 12 and through the clearance hole 66 (FIG. 4) extending radially through the bushing 43 from its longitudinal bore 44 to its outer peripheral surface 46. The inner end of the thumb screw 64 is preferably fitted with a tip 68 of nylon or other suitable wear resistant material for bearing against the outer surface of the shaft 22. It will be appreciated that as the thumb screw 64 is rotated and moves inwardly of the sleeve 12, the tip 68 eventually engages the outer surface of the shaft 22 and with continued rotation of the thumb screw 64, relative movement between the shaft and the sleeve 12 is effectively prevented. Locking mechanism 62 may thus be employed when it is desirable for the operator of the hand tool 10 to temporarily discontinue operation of the tool while retaining the relative position between the shaft and the sleeve.

In operation, an intramedulary pin 38 is inserted into the hand tool 10, then clamped by the chuck mechanism 32. The pin may be of any desirable length and, indeed, may be longer than the hand tool 10 itself such that it extends through the opening 16 at the upper end of the sleeve 12. The operator, who may be a physician or a veterinarian, grips the handle portion 21 of the sleeve 12 with one hand and presents the foremost tip of the intramedulary pin 38 to the bone structure to be united. Only one hand being required to operate the hand tool 10, the other hand of the operator is free to hold and adjust the object on which he is working. Force is then applied on the sleeve 12 in the direction of the bone structure to be united and in the direction of the longitudinal axis of the hand tool 10 and the intramedulary pin 38. As force is applied to the sleeve 12, the hollow shaft 22 is caused to rotate and, with it, the chuck mechanism 32 and the intramedulary pin 38. The spring 42 serves as a cushion between the sleeve 12 and the hollow shaft 22 and preferably has a spring rate chosen in accordance with the hardness of the bone structure being united. In the event it becomes desirable to delay the procedure once it has begun, by means of the locking mechanism 62, it is possible to hold the sleeve 12 and the shaft 22 in the relative positions they had assumed up to the time of the delay. Thereafter, the locking mechanism 62 can just as easily be released when the procedure is to be resumed.

When the procedure has been completed, whatever remains of the intramedulary pin 38 can be removed from the jaws 34 of the chuck mechanism 32. Thereupon, the hand tool 10 can be entirely disassembled in a simple and rapid fashion. Preferably all of the parts comprising the hand tool 10 are composed of stainless steel and Teflon or other non-corrosive materials suitable for sterilization. The parts can then be sterilized in any suitable fashion and thereafter reassembled for a future procedure.

The invention, then, in its broader aspects is not limited to the specific details shown and described and departures may be made from such details without departing from the principles of the invention, and with sacrificing its chief advantages.

What is claimed is:

1. A hand tool comprising:
   an elongated hollow sleeve open at its opposite ends including flange means adjacent one of said ends projecting into the interior thereof;
   a hollow shaft removably supported within said sleeve and substantially coaxial therewith having at least one continuous spiral groove in its outer surface intermediate its ends;
   follower means removably secured to said sleeve and slideably engagable with the spiral groove on said shaft to effect rotation of the shaft in response to relative longitudinal movement between said sleeve and said shaft;
   chuck means having an axial opening therethrough and removably mounted to one end of said shaft for releasably clamping an elongated pin for rotation with said shaft, said shaft having a longitudinal bore therethrough communicating with the axial opening in said chuck means; and
   resilient means extending between said flange means and an end of said shaft opposite said chuck means.

2. A hand tool as set forth in claim 1 wherein said follower means includes a bushing having a central bore extending therethrough and an outer peripheral surface and at least partially receivable within an end of said hollow sleeve opposite said flange means and a set screw threadedly engaged with said hollow sleeve and selectively engagable with said outer peripheral surface to releasably secure said bushing to said hollow sleeve.

3. A hand tool as set forth in claim 2 wherein said bushing has a slot extending radially therethrough from its central bore to said outer peripheral surface and including a key within the slot and engaged with said spiral groove.

4. A hand tool as set forth in claim 2 wherein said bushing is fabricated of polytetrafluoroethylene.

5. A hand tool as set forth in claim 1 wherein at least a portion of the axial opening of said chuck means is threaded and wherein one end of said hollow shaft is a stud threadedly engaged with the axial opening of said chuck means.

6. A hand tool as set forth in claim 1 including a support bushing freely mounted on an end of said hollow shaft opposite said chuck means, said resilient means extending between said flange means and said bushing.

7. A hand tool as set forth in claim 6 wherein said support bushing is fabricated of polytetrafluoroethylene.

8. A hand tool as set forth in claim 1 wherein said resilient means is a spring substantially coaxial with said sleeve and said shaft, said spring being selectively removable from said sleeve and replaceable by another spring having a different spring rate.

9. A hand tool as set forth in claim 1 including locking means selectively operable for holding said hollow shaft and said hollow sleeve against relative movement.

* * * * *